United States Patent
De Haan et al.

(10) Patent No.: US 9,615,581 B2
(45) Date of Patent: *Apr. 11, 2017

(54) STABLE NEEDLE-SHAPED CRYSTALS OF NATAMYCIN

(71) Applicant: DSM IP ASSETS B.V., Heerlen (NL)

(72) Inventors: Ben Rudolf De Haan, Echt (NL); Ferdinand Theodorus Jozef Van Rijn, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/729,542

(22) Filed: Jun. 3, 2015

(65) Prior Publication Data

US 2015/0264931 A1    Sep. 24, 2015

Related U.S. Application Data

(62) Division of application No. 12/926,283, filed on Nov. 8, 2010, now Pat. No. 9,096,633, which is a division of application No. 12/662,409, filed on Apr. 15, 2010, now Pat. No. 8,420,609, which is a division of application No. 11/665,155, filed as application No. PCT/EP2005/055592 on Oct. 27, 2005, now Pat. No. 7,727,966.

(30) Foreign Application Priority Data

Oct. 28, 2004  (EP) .................................... 04105363

(51) Int. Cl.
| | |
|---|---|
| *A01N 43/04* | (2006.01) |
| *A61K 31/70* | (2006.01) |
| *A01N 43/90* | (2006.01) |
| *A23G 9/36* | (2006.01) |
| *A23L 3/3463* | (2006.01) |
| *C07H 17/08* | (2006.01) |

(52) U.S. Cl.
CPC ............. *A01N 43/90* (2013.01); *A23G 9/366* (2013.01); *A23L 3/34635* (2013.01); *C07H 17/08* (2013.01); *A23V 2002/00* (2013.01); *Y10T 428/298* (2015.01); *Y10T 428/2982* (2015.01)

(58) Field of Classification Search
None
See application file for complete search history.

(56) References Cited

U.S. PATENT DOCUMENTS

| | | | |
|---|---|---|---|
| 3,343,968 A | 9/1967 | Huhtanen | |
| 3,378,441 A | 4/1968 | Bridger | |
| 4,148,891 A | 4/1979 | Smink | |
| 4,826,822 A | 5/1989 | Anderson et al. | |
| 5,552,151 A | 9/1996 | Noordam et al. | |
| 5,597,598 A | 1/1997 | Van Rijn et al. | |
| 5,686,273 A | 11/1997 | Eisenchink et al. | |
| 5,821,233 A | 10/1998 | Van Rijn et al. | |
| 5,942,611 A | 8/1999 | Borden et al. | |
| 5,962,510 A | 10/1999 | De Haan et al. | |
| 6,146,675 A | 11/2000 | Cirigliano et al. | |
| 6,150,143 A | 11/2000 | Raghoenath et al. | |
| 6,655,081 B1 | 12/2003 | Stark et al. | |
| 7,816,332 B2 | 10/2010 | Stark et al. | |

FOREIGN PATENT DOCUMENTS

| | | |
|---|---|---|
| GB | 1 470 005 | 4/1977 |
| WO | WO 92/10580 | 6/1992 |
| WO | WO 95/07998 | 3/1995 |
| WO | 9508918 A1 | 4/1995 |
| WO | WO 95/08918 | 4/1995 |
| WO | WO 95/27073 | 10/1995 |
| WO | 9729207 A1 | 8/1997 |
| WO | WO 97/29207 | 8/1997 |
| WO | WO 2006/045831 A1 | 5/2006 |

OTHER PUBLICATIONS

Tiwary, "Modification of Crystal Habit and Its Role in Dosage Form Performance," Drug Development and Industrial Pharmacy, 27(7), 699-709 (2001).
Ahmed et al., "Effect of Surfactants on the Crystal Properties and Dissolution Behavior of Aspirin," Asian J. Research Chem. 2(2), 202-206, Jul.-Sep. 2009.
Tsung et al., Crystallization of Organic Compounds, An Industrial Perspective, published by John Wiley & Sons, Inc., Hoboken, New Jersey, Jun. 2009, pp. 42 and 44.
Blagden et al., "Crystal engineering of active pharmaceutical ingredients to improve solubility and dissolution rates," Advanced Drug Delivery Reviews, 59(2007) 617-630.
Harry Brik, "Natamycin"; Analytical Profile of Drug Substances; vol. 10, 1981, pp. 513-561.
Database Biosis, Biosciences Information Service, 1978, XP-002254989.
International Search Report.
U.S. Appl. No. 10/558,701, filed Nov. 30, 2005.
Written Opinion and International Search Report mailed Feb. 16, 2006 in PCT/EP2005/055592.
Chaumeil, J.C. (1998) Micronization: A Method of Improving the Bioavailability of Poorly Soluble Drugs.
Methods and Findings in Experimental & Clinical Pharmacology, vol. 20, No. 3, pp. 211-215.

*Primary Examiner* — Patrick Lewis
(74) *Attorney, Agent, or Firm* — McBee Moore Woodward & Vanik IP, LLC

(57) ABSTRACT

The present invention describes natamycin comprising needle shaped crystals.

13 Claims, No Drawings

STABLE NEEDLE-SHAPED CRYSTALS OF NATAMYCIN

CROSS REFERENCE TO RELATED APPLICATIONS

This application is a divisional of U.S. Ser. No. 12/926,283, filed Nov. 8, 2010, which is a divisional of U.S. Ser. No. 12/662,409, filed Apr. 15, 2010, now U.S. Pat. No. 8,420,609, which is a divisional of U.S. Ser. No. 11/665,155, filed Apr. 12, 2007, now U.S. Pat. No. 7,727,966, which is a 371 National Stage of PCT/EP2005/055592, filed 27 Oct. 2005, which claims priority to EP 04105363.8, filed 28 Oct. 2004, the contents of which are incorporated herein by reference in their entireties.

The present invention relates to natamycin. For more than 20 years, natamycin has been used to prevent growth of mould on cheeses and sausages. Cheeses are treated by immersion in a suspension of natamycin in water or covered by an emulsion of a polymer (mostly polyvinyl acetate) in water containing natamycin. Sausages are mainly treated by immersion or by spraycoating with a suspension of natamycin in water. Usually aqueous suspensions for immersion treatments contain 0.1 to 0.2% (w/v) of natamycin, while polymer emulsions for coating purposes contain 0.01 to 0.05% (w/v) of natamycin.

For the production of such suspensions or polymer emulsions, the natamycin may be added directly to the liquids as a powder, for instance by using the wettable powder composition known under the brand name of Delvocid® Instant. Instead of using the powder as such, frequently a concentrated presuspension of the natamycin in water is prepared before adding the natamycin to the liquids to be used for treatments. The purpose of preparing a presuspension is to avoid lump formation and to facilitate homogenisation of natamycin through the treatment liquids. Mostly these methods of preparing suspensions for treating food are adequate. However, when several types of suspension with varying concentrations of natamycin have to be prepared or several portions of large quantities need to be produced over a longer period such methods are less convenient.

When natamycin is added as a powder to treatment preparations, the laborious weighing of the powder has to be repeated for each type of suspension, which multiplies the number of possible nuisances.

When a presuspension in water is used to avoid inaccurate dosages, the presuspension has to be agitated continuously to prevent the natamycin from settling down or the presuspension has to be added in total to the treatment preparations.

Aqueous suspensions of natamycin are well known in practice. Under the brand name of Pimafucin®, sterile suspensions of natamycin are commercially available as a 1% or a 2.5% presentation in small bottles of up to 100 ml. Pimafucin® is mainly used for medical purposes. To render these suspension suitable as a multiple dose presentation, the suspensions are preserved by using benzalkonium chloride, a preservative of the quaternary ammonium type. Because of the sedimentation of the solid natamycin during storage, such a suspension has to be shaken well every time prior to use.

As mentioned above, natamycin present in a suspension (as well as in a presuspension) tends to settle down to form a sediment at the bottom of a container. In case the suspension is not agitated continuously a sediment will be formed on the bottom which is only very difficult to bring back into the suspended state.

The objective of the invention is to provide a natamycin that does not settle down very quickly and/or that is easy to resuspend.

DESCRIPTION

The present invention provides a new form of natamycin crystals, which are in a needle-shaped form. According to a first aspect, the invention relates to natamycin comprising needle shaped crystals. The needle-shaped crystals of the invention are particularly well-suited to be used in suspensions. A sediment of the crystals of the invention are more easily brought back into the suspended state than other type of natamycin having other crystal type. The natamycin crystals according to the invention have a needle or cylindrical form. Preferably, the natamycin of the invention comprises at least 90% w/w (anhydrous basis) of needle shaped crystals as defined below. More preferably, at least 95% of needle shaped crystals, even more preferably at least 95% and most preferably at least 98%.

The mean length of needle shaped crystals will in general be between 0.1 and 20 µm. Preferably, the crystals having a needle shaped form have a length of more than 2 µm, more preferably have a length of more than 4 µm, most preferably have a length of more than 6 µm. Preferably, the mean diameter of the needle shaped crystals is between 0.1 and 2 µm, more preferably less than 1.5 µm and most preferably a length of less than 1.0 µm. By "length" and "diameter" is meant the length and diameter as measured with an (Olympus) microscope (type BH-2) with a total used magnification of 1000 times, whereby the length is the largest length size of the crystal and the diameter is the size of the thickness of the crystal measured in the middle of the length and perpendicular to the length direction. The mean length and the mean diameter are both determined by measuring at least 100 crystals. The needle-shaped crystal form of natamycin is different from the presently known forms of natamycin. The known natamycin crystals have in general a plate-like form. By plate-like is meant a form whereby the length and width are of the same order of dimension, which is in general 10 times higher than the thickness of the plate crystals.

Although the plate and needle crystals of the natamycin have a completely different form, the crystal lattice is for both forms the same. This crystal lattice is often indicated as Alpha-natamycin. The present invention preferably relates to needle-shaped crystals of Alpha-natamycin.

According to another aspect of the present invention, there is provided a process to produce the needle-shaped crystals of the invention. In the first step of this process, natamycin is dissolved in an aqueous solution. The solution comprises at least 80 wt %, preferably at least 90 wt % more preferably at least 95 wt % and still more preferably at least 98 wt % and preferably at least 99 wt % water as solvent. Although at neutral pH, natamycin will hardly dissolve in water, at low pH, e.g. at a pH lower than 4.0 preferably between 1.0 and 3.0 or at high pH, e.g. at a pH above 10.0, preferably between 10.0 and 14.0, natamycin will easily dissolve in water. Preferably, natamycin is dissolved at a pH ranged between 10 and 14, more preferably at a pH ranged between 11 and 13. In general, natamycin of a purity of more than 90 wt % (including hydrate) preferably of a purity of 95% is used. It is found that also natamycin with lower purity can be used in the process of the invention.

In general, the natamycin solution will contain 1 to 300 g/l of natamycin, preferably 5 to 200 g/l and most preferably 10 to 100 g/l of natamycin. After that a dissolved natamcyin solution has been obtained, the pH is brought to neutral. In general the pH will be brought to a pH ranged between 4 and 10, preferably to a pH ranged between 5 and 9 and more preferably between 6 and 8. Lowering the pH can for example be done with HCl. Increasing the pH can for example with NaOH. But also other suitable acids or bases can be used in the process of the invention.

During the pH neutralisation, the crystals according to the present invention are formed. During the addition of acid or base the liquid is preferably stirred to prevent that local pH difference will occur. Typically, the addition of the acid or base to the dissolved natamycin solution to form the suspension of natamycin at neutral pH will take 5 to 50 minutes, preferably 10 to 30 minutes. We noted that shorter times, for example 1 minute does not always result in needles but more or less in lump-like natamycin possibly due to local pH variations. Times of more than 1 hour are possible and suitable needles are also formed, but longer times are economically less attractive. The temperature of the solution or suspension is kept in general between 5° C. and 35° C., preferably between 15° and 25° C. The crystallized needles can be dried or can be used as such. Preferably the crystals and the liquid phase are not separated but can be used or stored as a suspension. According to the method of the invention, preferably the solvent used in the process of the invention comprises art least 90 wt % water. More preferably the solvent comprises at least 95 wt % of water, even more preferably at least 98 wt % water, even more preferably at least 99 wt % water and most preferably 100 wt % of water. The needles formed preferably comprise less than 5 ppm, more preferably less than 1 ppm of a solvent other than water. Preferably, the crystals contain less than 5 ppm of an alcohol such as methanol, more preferably less than 1 ppm of alcohol such as methanol.

Herein above is mentioned that preferably natamycin of more than 90 wt % purity is used. This wt % includes the hydrate or metal salt form of natamycin. This wt % purity is based on the compounds as obtained after fermentation or recovery or purification of natamycin and addition of other compounds are not included in this calculation. For example, when a 50% natamycin product is sold which also includes 50% of a filler such as lactic acid, this filler is not included in the purity figure.

As discussed above a sediment of the needle-shaped crystals of the present invention can be easily brought back in the suspended state without exclusive stirring or shaking. Another advantage of the needle-shaped crystals is that this crystal form is stable. For example it is found that after 6 months of storage of a needle-shaped crystal suspension, which was stored at 10° C., the suspension still contained needle-shaped crystals having the same mean length.

Another surprising effect of the crystals of the present invention is that when the suspension is supplied to a surface to be coated with the suspension, the surface distribution of the natamycin crystals is improved in the sence that because of the special needle-shaped crystals compared to plate like crystals local concentrations (on micron-scale) are more uniform.

The natamycin of the invention and any composition comprising the natamycin of the invention can be used for any type of applications in food products, agricultural products, cosmetic products or pharmaceutical products.

According to a further aspect, the invention relates to a composition comprising the natamycin of the invention. The composition may be a liquid composition, a coating emulsion, a dry formulation such as a powder, a granulate or a tablet.

The amount of natamycin, in a liquid composition may be from 0.001% to 2% w/w. Preferably, the amount is from 0.01% to 1% w/w. Preferably, the liquid composition is used in an immersion treatment or a spraying treatment. In principle, the immersion liquid may be of any kind. When an aqueous system is used, the addition of a surfactant may be of advantage, in particular for treating objects with a hydrophobic surface.

In a coating emulsion according to the invention, the amount of natamycin, may be from 0.001% to 2% w/w, preferably from 0.01% to 1% w/w and more preferably from 0.01% to 0.5% w/w. The coating emulsion may be of the o/w or w/o type. Particularly preferred are emulsions prepared from coating emulsions commonly employed in the food industry. For example, for the treatment of hard cheeses an aqueous polymer emulsion of the polyvinyl acetate type may be used.

In a dry formulation according to the invention, the amount of natamycin may be from 1% to 95% w/w, preferably from 10% to 70% w/w, more preferably from 30% to 55% w/w.

A composition comprising natamycin can be added to the product to be treated at any moment or step of the processing. The composition can be added in the end product before packaging, during processing or in any ingredients used to prepare the products. The advantage of the present invention is that it allows the production of microbiologically stable and safe products with low concentration of anti-microbials. The innovative composition can be used to preserve microbiological safety and/or stability in all kind of products. Preferably the product is a food product such as dairy products, dairy desserts such as ice cream mixes, yoghurt, or cottage cheese, ricotta, cream cheese, sour cream. Other preferred food products are hot-baked flour products, spreads, margarines, sauce, dressings or any other foodstuffs distributed at ambient or chilled temperatures. Other preferred food products are beverages like fruit juice, wine. Preferred food products have pH ranging from pH 2.0 to pH 7.0. The addition of the composition of the invention comprising natamycin to food products is furthermore expected to reduce or completely eliminate moulds, yeasts and bacterial outgrowth on the food products in the time frame comprised between the end of the processing of the product, size reduction included and commercial sale. This time frame varies with the type of food, the distribution and sale conditions. Preferably, the product to be treated is such that its surface will be in contact with oxygen at the end of its processing and/or later on if a reduction of size occurs.

According to another preferred embodiment, the composition comprising the natamycin of the invention is a composition suitable for treating agricultural products such as fruits, vegetable and seed. Preferred fruits are citrus fruit, bananas, ananas, strawberry and the like.

According to another preferred embodiment, the composition comprising the natamycin of the natamycin of the invention is a pharmaceutical preparation suitable for topical application. Examples of suitable pharmaceutical preparations are lotions, creams and ointments.

According to another preferred embodiment, the anti-microbial composition of the invention comprising natamycin has a pH ranging from pH 2.0 to pH 7.0, more preferably from 3.0 to 5.0. According to another preferred embodiment, the anti-microbial composition of the invention further comprises water and/or salt and/or any component selected from the group consisting of a solvent, a surfactant, a carrier, a food acid, a thickener, any other food grade anti-microbial compound. Preferred solvents, surfactants and carrier are already described in WO 95/08918. Preferred carrier is fumed silica. Preferred solvents are an alcoholic solvent comprising one or more lower alcohols (C1-C4), an aqueous acid, an aqueous alkali, glacial acetic acid or mixtures of an alcoholic solvent comprising one or more lower alcohol with either an aqueous acid, an aqueous alkali or glacial acetic acid. Preferred surfactants are sodium lauryl sulphate, dioctyl sulphosuccinate, calcium chloride, or surfactants of the non-ionic types, for example those which are known under the brand names Tween, Span, Brij, and Myrj. Preferred thickeners may be any thickener known in the art for use in food products. Preferred thickeners are hydroxypropylmethylcellulose (HPMC), and/or gums, and/or carrageenan and/or methylcellulose. Preferred gums are xanthan gum and/or gellan gum and/or arabic gum as described in U.S. Pat. No. 5,962,510 or U.S. Pat. No. 5,552,151. Preferred food acids are organic acidic anti-fungal agent such as benzoic acid, propionic acid or sorbic acid or other acids such as acetic acid or lactic acid as described in EP 608 944 B1.

According to a further aspect of the invention, a product is provided which has been treated with the natamycin of the invention or with the composition of the invention including the natamycin of the invention.

According to another preferred embodiment, the product is a water-containing product for example a food product, which comprises the natamycin of the invention or the composition of the invention including natamycin.

According to a further aspect of the invention, there is provided the use of the natamycin of the invention to obtain a product, for example a food product, comprising the composition of the invention including natamycin.

According to a further aspect of the invention, there is provided a method for treating a product, for example a food product, with the natamycin of the invention or which comprises the composition of the invention including the natamycin of the invention.

According to a further aspect, the invention relates to a method for protecting a product against fungal spoilage by applying the natamycin of the invention or the composition of the invention including the natamycin of the invention.

Before, during or after the addition of natamycin to the product, other ingredients such as colorants, texturals etc. can be added as well to the product.

The invention will further now be illustrated by examples, which should not be construed as limiting the scope of the invention.

EXAMPLES

Material and Methods

Materials

Delvocid® containing 50% active (w/w) natamycin, DSM Food Specialties, (P.O. Box 1, 2600 MA, Delft, The Netherlands).

Hydrochloric acid, purchased from Gaches Chimie France, (31750 Escalquens, France).

Sodium hydroxide, purchased from Gaches Chimie France, (31750 Escalquens, France).

Example 1

This example describes a method to prepare a concentrate dispersion of natamycin with needle shaped crystals suitable to be used as test material in direct comparison to standard natamycin crystals.

A suspension of natamycin was prepared by suspending 150 gram Delvocid® in 4000 gram water while stirring with an electric top stirrer, type RW 20 DZM, from Janke & Kunkel equipped with a rushton stirrer. While stirring, 600 ml 4M NaOH solution is added to a final pH of ±12 resulting in a clear light yellow liquid. Directly after obtaining a clear liquid, 600 ml 4M HCl solution was added in 20 minutes time to a final pH of 6.5. During addition of the HCl, a haze appeared and finally the liquid changed to a very viscous suspension.

This suspension was used as starting material for the other described examples.

We have found that the use of destilled or tap water (Delft, Holland or St. Clar (near Toulouse) France) did not have an influence on the needle formation.

Example 2

This example describes another method to prepare a concentrate dispersion of natamycin with needle shaped crystals. A suspension of natamycin was prepared by suspending 150 gram Delvocid® in 4000 gram water while stirring with an electric top stirrer, type RW 20 DZM, from Janke & Kunkel equipped with a rushton stirrer. While stirring, 4M HCL was added to a final pH of 0.8 resulting in a clear light yellow liquid. Directly after obtaining a clear liquid, 4M NaOH was added slowly to a final pH of ±6.5. During addition of the NaOH, a haze appeared and finally the liquid changed to a very viscous suspension. The obtained crystals had similar characteristics as the crystals obtained in Example 1.

Example 3

This example describes the method that was used to analyze the amount of active natamycin in a water-based mixture of several components.

The method used was a HPLC analysis based on the International Dairy Federation (Provisional IDF Standard 140, 1992) with a Lichrosorb RP 8 column.

Detection was at 303 nm UV with a range of 0.1-4 mg/L with an injection volume of 20 µl. Sample preparation was carried out by weighing 2 g of prepared formulation with an accuracy of 1 mg in a measuring flask. 4 ml demineralized water (demiwater) was added and the mixture was stirred for 15 minutes to get a homogeneous suspension.

Subsequently, 80 ml ethanol was added and the mixture was stirred for 10 minutes.

After ultrasonic treatment, the solution was filled up to 100 ml with demiwater and then diluted and/or filtered (0.2 µm) before injecting. The amount of active natamycin was calculated as ppm against a series of standards.

Example 4

This example describes the test performed to analyze the sedimentation differences.

1.5 g Delvocid® was added to 998.5 gram tapwater and dispersed well by an electric top stirrer, type RW 20 DZM, from Janke & Kunkel equipped with a rushton stirrer.

1.5 gram of Delvocid® made according to Example 1 was mixed with tapwater to a final weight of 1000 gram by an electric top stirrer, type RW 20 DZM, from Janke & Kunkel equipped with a rushton stirrer.

Both homogeneous mixtures were poured in glass tubes and observed in time on demixing.

The results are set out in Table 1.

TABLE 1

| Time (minutes) | Standard natamycin | Recrystallized natamycin |
| --- | --- | --- |
| 0 | Homogeneous | Homogeneous |
| 40 | Start demixing observed | Homogeneous |
| 60 | Two layers observed | Homogeneous |
| 110 | Pellet formation | Homogeneous |
| 180 | Pellet formation | Homogeneous |
| 4320 | Pellet and clear top layer | Start demixing observed |

Example 5

This example describes the test that was performed to analyze the resuspendability of settled natamycin in a low viscous dispersion. 1.5 gram Delvocid® was added to 998.5 gram tapwater and dispersed well by an electric top stirrer, type RW 20 DZM, from Janke & Kunkel equipped with a rushton stirrer. An amount equal to 1.5 gram Delvocid® made according to Example 1 was mixed with tapwater to a final weight of 1000 gram by an electric top stirrer, type RW 20 DZM, from Janke & Kunkel equipped with a rushton stirrer. Both homogeneous mixtures were poured in glass tubes and not touched for 26 days. After 26 days, the glass tubes were turned around once and it was observed that the pellet of the recrystallized natamycin was almost completely resuspended and that the pellet of the standard natamycin remained a solid pellet.

Example 6

This example describes the stability of recrystallized natamycin, a natamycin dispersion is made according to Example 1 and followed in time on stability.

The rest activity of natamycin is set out in Table 2.

TABLE 2

| Incubation time (months) | Found natamycin activity (%) |
| --- | --- |
| 0 | 100 |
| 1 | 100 |
| 2 | 99 |
| 4 | 100 |
| 6 | 98 |

The stability of the recrystallised natamycin is very high for at least six months.

The invention claimed is:

1. A method for the reduction of mold, yeast, and bacterial outgrowth on a food product comprising treating the food product with needle shaped crystals of α-natamycin having a mean length of between 0.1 and 20 μm.

2. The method according to claim 1, wherein said food product is selected from the group consisting of a dairy product, a dairy dessert, a hot-baked flour product, a spread, a margarine, a sauce, a dressing, and a beverage.

3. The method according to claim 2, wherein said dairy product is selected from the group consisting of an ice cream mix, a yoghurt, cottage cheese, ricotta, cream cheese, and sour cream.

4. The method according to claim 2, wherein said beverage is selected from the group consisting of fruit juice and wine.

5. The method according to claim 1, wherein 60% of the needle shaped crystals have a length of more than 2 μm.

6. The method according to claim 1, wherein the needle shaped crystals have a mean diameter of between 0.1 and 2 μm.

7. The method according to claim 1, wherein 60% of the needle shaped crystals have a diameter of less than 2 μm.

8. A pharmaceutical preparation comprising needle shaped crystal of α-natamycin having a mean length of between 0.1 and 20 μm, wherein said pharmaceutical preparation is suitable for topical application.

9. The pharmaceutical preparation of claim 8, wherein said pharmaceutical preparation is selected from the group consisting of a lotion, a cream, and an ointment.

10. The pharmaceutical preparation of claim 8, wherein 60% of the needle shaped crystals have a length of more than 2 μm.

11. The pharmaceutical preparation of claim 8, wherein the needle shaped crystals have a mean diameter of between 0.1 and 2 μm.

12. The pharmaceutical preparation of claim 8, wherein 60% of the needle shaped crystals have a diameter of less than 2 μm.

13. The pharmaceutical preparation of claim 8, wherein said pharmaceutical preparation further comprises a component selected from the group consisting of water, a solvent, a salt, a surfactant, a carrier, a food acid selected from the group consisting of benzoic acid, propionic acid, sorbic acid, acetic acid, and lactic acid, a thickener, and a food grade antimicrobial compound.

* * * * *